United States Patent [19]

Martin et al.

[11] Patent Number: 5,510,330

[45] Date of Patent: Apr. 23, 1996

[54] COMBINATIONS OF THROMBOLYTICALLY ACTIVE PROTEINS AND NON-HEPARIN ANTICOAGULANTS, AND USES THEREOF.

[75] Inventors: Ulrich Martin, Mannheim; Stephan Fischer, Polling, both of Germany

[73] Assignee: Boehringer Mannheim GmbH, Mannheim, Germany

[21] Appl. No.: 217,618

[22] Filed: Mar. 25, 1994

[51] Int. Cl.[6] .......................... A61K 38/00; A61K 38/48
[52] U.S. Cl. .......................... 514/12; 435/212; 435/215; 435/216; 435/226; 424/94.63; 424/94.64
[58] Field of Search .............................. 424/94.63, 94.64; 514/12; 435/212, 215, 216, 226

[56] References Cited

U.S. PATENT DOCUMENTS

| | | | |
|---|---|---|---|
| 4,970,159 | 11/1990 | Dodd | 435/226 |
| 4,980,165 | 12/1990 | Isaacs et al. | 424/94.64 |
| 5,049,132 | 9/1991 | Shaffer | 604/101 |
| 5,084,274 | 1/1992 | Griffin et al. | 424/94.64 |
| 5,126,134 | 6/1992 | Heim et al. | 424/94.64 |
| 5,189,019 | 2/1993 | Paladino et al. | 514/12 |
| 5,196,404 | 3/1993 | Maraganore et al. | 514/12 |
| 5,204,323 | 4/1993 | Findlay et al. | 512/12 |
| 5,223,256 | 6/1993 | Stern et al. | 424/94.64 |
| 5,240,913 | 8/1993 | Maraganore et al. | 514/12 |
| 5,242,688 | 9/1993 | Burck et al. | 424/94.64 |
| 5,242,810 | 9/1993 | Maraganore et al. | 435/69.2 |
| 5,350,578 | 9/1994 | Griffin et al. | 424/94.64 |

*Primary Examiner*—Herbert J. Lilling
*Attorney, Agent, or Firm*—Felfe & Lynch

[57] ABSTRACT

The invention involves thromboembolically effective compositions and therapeutic methods. Thrombolytically active proteins are combined with anticoagulants, as long as the anticoagulant is not heparin. The anticoagulant is administered in an intravenous bolus form, while the thrombolytically active protein may be administered via intravenous bolus, or intravenous infusion.

10 Claims, 5 Drawing Sheets

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 355 amino acids
( B ) TYPE: amino acids
( C ) TOPOLOGY: linear ( x i ) SEQUENCE DESCRIPTION: SEQ ID NO: 1:

```
Ser  Tyr  Gln  Gly  Asn  Ser  Asp  Cys  Tyr  Phe  Gly  Asn  Gly  Ser  Ala  Tyr
                    5                        10                       15
Arg  Gly  Thr  His  Ser  Leu  Thr  Glu  Ser  Gly  Ala  Ser  Cys  Leu  Pro  Trp
                   20                        25                       30
Asn  Ser  Met  Ile  Leu  Ile  Gly  Lys  Val  Tyr  Thr  Ala  Gln  Asn  Pro  Ser
                   35                        40                       45
Ala  Gln  Ala  Leu  Gly  Leu  Gly  Lys  His  Asn  Tyr  Cys  Arg  Asn  Pro  Asp
          50                        55                       60
Gly  Asp  Ala  Lys  Pro  Trp  Cys  His  Val  Leu  Lys  Asn  Arg  Arg  Leu  Thr
 65                        70                       75                       80
Trp  Glu  Tyr  Cys  Asp  Val  Pro  Ser  Cys  Ser  Thr  Cys  Gly  Leu  Arg  Gln
                    85                       90                       95
Tyr  Ser  Gln  Pro  Gln  Phe  Arg  Ile  Lys  Gly  Gly  Leu  Phe  Ala  Asp  Ile
```

|     |     |     |     |     |     |     |     |     |     |     |     |     |     |     |
|-----|-----|-----|-----|-----|-----|-----|-----|-----|-----|-----|-----|-----|-----|-----|
|     |     |     | 100 |     |     |     |     | 105 |     |     |     | 110 |     |     |
| Ala | Ser | His 115 | Pro | Trp | Gln | Ala | Ala 120 | Ile | Phe | Ala | Lys | His 125 | Arg | Arg | Ser |
| Pro | Gly 130 | Glu | Arg | Phe | Leu | Cys 135 | Gly | Gly | Ile | Leu | Ile 140 | Ser | Ser | Cys | Trp |
| Ile 145 | Leu | Ser | Ala | Ala | His 150 | Cys | Phe | Gln | Glu | Arg 155 | Phe | Pro | Pro | His | His 160 |
| Leu | Thr | Val | Ile | Leu 165 | Gly | Arg | Thr | Tyr | Arg 170 | Val | Val | Pro | Gly | Glu 175 | Glu |
| Glu | Gln | Lys | Phe 180 | Glu | Val | Glu | Lys | Tyr 185 | Ile | Val | His | Lys | Glu 190 | Phe | Asp |
| Asp | Asp | Thr 195 | Tyr | Asp | Asn | Asp | Ile 200 | Ala | Leu | Leu | Gln | Leu 205 | Lys | Ser | Asp |
| Ser | Ser 210 | Arg | Cys | Ala | Gln | Glu 215 | Ser | Ser | Val | Val | Arg 220 | Thr | Val | Cys | Leu |
| Pro 225 | Pro | Ala | Asp | Leu | Gln 230 | Leu | Pro | Asp | Trp | Thr 235 | Glu | Cys | Glu | Leu | Ser 240 |
| Gly | Tyr | Gly | Lys | His 245 | Glu | Ala | Leu | Ser | Pro 250 | Phe | Tyr | Ser | Glu | Arg 255 | Leu |
| Lys | Glu | Ala | His 260 | Val | Arg | Leu | Tyr | Pro 265 | Ser | Ser | Arg | Cys | Thr 270 | Ser | Gln |
| His | Leu | Leu 275 | Asn | Arg | Thr | Val | Thr 280 | Asp | Asn | Met | Leu | Cys 285 | Ala | Gly | Asp |
| Thr | Arg 290 | Ser | Gly | Gly | Pro | Gln 295 | Ala | Asn | Leu | His | Asp 300 | Ala | Cys | Gln | Gly |
| Asp 305 | Ser | Gly | Gly | Pro | Leu 310 | Val | Cys | Leu | Asn | Asp 315 | Gly | Arg | Met | Thr | Leu 320 |
| Val | Gly | Ile | Ile | Ser 325 | Trp | Gly | Leu | Gly | Cys 330 | Gly | Gln | Lys | Asp | Val 335 | Pro |
| Gly | Val | Tyr | Thr 340 | Lys | Val | Thr | Asn | Tyr 345 | Leu | Asp | Trp | Ile | Arg 350 | Asp | Asn |
| Met | Arg | Pro 355 |     |     |     |     |     |     |     |     |     |     |     |     |     |

COMBINATIONS OF THROMBOLYTICALLY ACTIVE PROTEINS AND NON-HEPARIN ANTICOAGULANTS, AND USES THEREOF.

FIELD OF THE INVENTION

The present invention relates to compositions and methods for treatment of patients with acute occlusive vascular diseases. These are characterized by administration of an anticoagulant agent which is not heparin via i.v. bolus injection instead of prolonged intravenous infusion, in combination with thrombolytically active protein which may be given by intravenous bolus injection and/or by intravenous infusion.

BACKGROUND AND PRIOR ART

Cardiovascular diseases, such as acute myocardial infarction, stroke, peripheral arterial occlusion, pulmonary embolisms, deep vein thrombosis, and other blood vessel thrombotic diseases are major causes of morbidity and mortality. The aforementioned diseases are caused by total or subtotal occlusive thrombus formation in a blood vessel, which prevents delivery of an adequate blood supply to the tissue. The thrombus consists of aggregates of blood cells such as platelets, erythrocytes, and leukocytes, stabilized by a fibrin network.

Current therapeutic approaches to these thrombotic vascular diseases involves lysis of the existing thrombus and prevention of recurrent thrombus formation, leading to reocclusion of the formerly reopened vessel.

Thrombolytic therapy of acute myocardial infarction has been shown to markedly improve the natural history of acute myocardial infarction, with an approximately 30% reduction in mortality (GISSI: Lancet 1986; 1: 871–874; ISIS-2: Lancet 1988; 2: 349–360; AIMS: Lancet 1988; 1: 545–549; Wilcox et al., Lancet 1988: 2: 525–539; ISAM: N Engl J Med 1986; 314: 1465–1471). The findings of the recently completed GUSTO-trial (Global Utilisation of Streptokinase and Tissue-type plasminogen activator for Occluded coronary arteries) indicated that accelerated t-PA given with intravenous (i.v.) heparin provided a survival benefit over previous standard thrombolytic regimens (GUSTO: N Engl J Med 1993; 329: 673–682). More importantly, the study supported the hypothesis that more rapid and complete restoration of coronary blood flow through the infarct-related artery resulted in improved ventricular performance and lower mortality among patients with myocardial infarction. (GUSTO; N Engl J Med 1993; 329: 1615–1622).

However, recent data suggest that current reperfusion strategies do not realize the maximum potential for reduction of mortality and salvage of ventricular function (Lincoff and Topol, Circulation 1993; 87: 1792–1805). The benefits of thrombolysis substantially deteriorate in many patients due to insufficiently early or rapid recanalization, incomplete patency with TIMI grade 3 flow or critical residual stenosis, absence of myocardial tissue reflow despite epicardial artery patency, intermittent coronary patency, subsequent reocclusion, or reperfusion injury. Therefore, there are efforts underway to achieve optimal reperfusion. These efforts are directed, for the most part, at enhancement of the velocity and quality of thrombolysis.

Pharmacological approaches to enhancing velocity and quality of thrombolysis can, in general, be based upon the thrombolytic agent itself and upon adjunctive agents, i.e., other agents given concomitantly to the thrombolytic agent.

Recombinant tissue-type plasminogen activator (rt-PA) has been shown to achieve higher patency rates resulting in lower mortality when a total dose of 100 mg was administered in an accelerated regimen, i.e., within 90 min, instead of in the conventional, approved 3-h regimen (ISIS-3: Lancet 1992: 339: 753–770; GUSTO: N Engl J Med 1993; 329: 673–682). Apart from modifying the administration regimen of rt-PA, the use of a novel thrombolytically active protein, such as the novel recombinant plasminogen activator BM 06.022, described in U.S. Pat. No. 5,223,256 and incorporated by reference was shown to achieve very high patency rates after double bolus administration (Bode et al., Circulation 1993; 88 (suppl. I): I-292, abstract 1562).

The problem of reocclusion of the infarct-related artery after successful reperfusion has been recognized to be associated with substantial morbidity and mortality rates (Ohman et al., Circulation 1990; 82: 781–791). Therefore, pharmacologic strategies aim at reducing reocclusion and sustaining infarcted artery patency. Since activation of platelets and of the coagulation system after administration of thrombolytic agents has been shown to be involved, for the most part, in the pathogenesis of reocclusion, attempts are being made to pharmacologically inhibit platelet aggregation and coagulation. Therefore, the use of aspirin, an antiplatelet agent, and of heparin, an anticoagulant agent, is usually recommended in combination with the thrombolytic agents when treating acute myocardial infarction (Popma and Topol, Ann Int Med 1991; 115: 34–44).

However, the efficacies of aspirin and heparin are limited. This is attributable to their modes of action. Aspirin only inhibits one pathway of activation of platelets (by inhibition of cyclooxygenase). The action of heparin is dependent on the availability of antithrombin III. The restricted efficacy of heparin is also caused by the presence of inhibitors in plasma and its limited access to clot-bound thrombin. Therefore, there is a great deal of interest in novel antiplatelet agents, such as antagonists of the glycoprotein IIb/IIIa receptor (e.g., antibodies, peptides, or low molecular weight chemical entities) and in novel anticoagulants (peptidic and synthetic direct inhibitors of thrombin and other components of the coagulation system, such as inhibitors of factor Xa, IXa, VIIa, tissue factor, etc., or mimics of endogenous inhibitors of the coagulation system, such as activated protein C or thrombomodulin).

Recently, clinical trials began evaluating the usefulness of combining t-PA with the chimeric 7E3 antibody, which binds to the glycoprotein IIb/IIIa receptor (Kleiman et al., J Am Coll Cardiol 1993; 22: 381–389). Several clinical trials have already been performed to study the effect of combination of a thrombolytic agent with novel direct inhibitors of the coagulation system. The combination of accelerated t-PA and hirudin (a recombinant protein which directly inhibits clot-bound thrombin) resulted in prevention of reocclusion and high TIMI grade III patency rates (Cannon et al., J Am Coll Cardiol 1993; 21: 136A and Neuhaus et al., Circulation 1993; 88 (suppl. I): 1–292, abstract 1563). The hirudin like peptide hirulog was combined with infusion of streptokinase; the study showed that clot lysis occurred more rapidly after streptokinase plus hirulog (Lidón et al., J Am Coll Cardiol 1993; 21: 419A).

Since the use of t-PA is associated with a high reocclusion rate (10–20%) after thrombolysis despite the use of aspirin and heparin (Neuhaus et al., J Am Coll Cardiol 1989; 14: 1566–1569; Cheseboro et al., Circulation 1987; 76: 142–154; Neuhaus et al., J Am Coll Cardiol 1988; 12: 581–587; Califf et al., Circulation 1991; 83: 1543–1556; Neuhaus et al., J Am Coll Cardiol 1992; 19: 885–891), the administration of the novel adjunctive agents hirudin and hirulog required prolonged infusion for 36, 48, or 96 h. This long infusion period means that huge amounts of recombinant protein (=hirudin) or synthetic peptide (=hirulog) are required: 532 or 546 mg of hirudin or 1008 mg of hirulog as calculated by multiplying the dose (mg/kg/h) with the mean body weight of a human (70 kg) and with the duration of infusion described in the above mentioned abstracts. Large amounts of protein or synthetic peptide are expensive which in turn leads to high costs and is medically disadvantageous, since the high price of the anticoagulant prevents widespread use. Furthermore, the administration of an infusion increases costs, since the technique requires infusion machines, monitoring of the anticoagulant effectiveness, and medical staff to control the infusion. These obstacles limit the broad use and application of hirudin and, thereby, many patients will not profit from its benefits.

The combined results of the materials GISSI-2 (Lancet 1990; 336: 65–71) and ISIS-2 (Lancet 1988; 2: 349–360) demonstrated a "significantly increased incidence of cerebral hemorrhage and major noncerebral bleeds with the addition of heparin to the thrombolytic/aspirin regimen" which is medically very disadvantageous (Lincoff and Topol, Circulation 1993; 87: 1792–1805). Since early clinical experience with hirudin indicated that spontaneous hemorrhaging occurred after administration of hirudin, t-PA, and aspirin and that there was an increase in catheter site bleeding (Neuhaus et al., Circulation 1993; 88 (suppl. I): I-292, abstract 1563), there seems to be no reduction of the bleeding risk when replacing heparin-infusion by hirudin-infusion.

Experimental evaluation of the effect of combining hirudin with a thrombolytically active protein has always been performed with infusion of hirudin. Exemplary are reports on t-PA plus hirudin (Haskel et al., Circulation 1991; 83: 1048–1056), streptokinase plus hirudin (Rigel et al., Circ Res 1993; 72: 1091–1102) and BM 06.022 SEQ ID NO: 1 plus hirudin (Martin et al., Int J Hematol 1992; 56: 143–153). All these experimental studies have shown that hirudin-infusion was superior to heparin-infusion in improving coronary blood flow after reperfusion. Administration of heparin as a single i.v. bolus injection plus the thrombolytic agent BM 06.022 SEQ ID NO: 1 was not superior to heparin-infusion plus BM 06.022 SEQ ID NO: 1 (Martin et al., J Am Coll Cardiol 1993; 22: 914–920).

Clinical experience has shown that reocclusion occurred from after reperfusion up to hospital discharge of the patient at 7–21 days after reperfusion, with a peak incidence within the first few days after thrombolysis (Ohman et al., Circulation 1990; 82: 781–791). This observation explains why potent anticoagulation has to be prolonged for several days after thrombolytic treatment.

Pharmacokinetic analysis showed that hirudin has a short half life of 10–15 min in dogs (Biomed Biochim Acta 1987; 46: 237–244 and Folia Haematol 1988; 115: 70–74) and of 9–50 min in humans (Thromb Haemost 1984; 52: 160–163).

The experimental, clinical, and pharmacokinetic data discussed supra suggest that it is necessary to administer anticoagulant by continuous i.v. infusion in order to achieve reliably adequate plasma levels for anticoagulation in the treatment of acute vascular diseases. Current clinical evaluation of hirudin as a novel anticoagulant in combination with thrombolytically active proteins follows this line of reasoning.

Notwithstanding these suggestions, there still exists a need to reduce the amount of protein, peptide, or chemical entity used in thrombolytic treatment, a need to simplify administration, and a need to reduce bleeding risk by restricting the potency and anticoagulant efficacy of a drug to an optimum. This optimum combines a desire for the maximum duration of the effect of improving coronary blood flow quality and the minimum duration of unwanted side effects such as minor and major bleeding events and intracerebral hemorrhage.

SUMMARY OF THE INVENTION

The present invention provides pharmaceutically compositions and methods for treatment of a patient with a thrombotic disease. According to the invention, the pharmaceutically effective compositions, and methods for treatment of a patient with a thrombotic disease are characterized by administration of an i.v. bolus injection instead of prolonged i.v. infusion of a potent and effective anticoagulant agent which is not heparin, in combination with a thrombolytically active protein, which may be given by i.v. bolus injection and/or i.v. infusion.

This method is useful because it reduces the amount of anticoagulant necessary without losing the desired pharmacological effect of enhancing reperfusion and preventing reocclusion. Thereby, and most surprisingly, this reduces the bleeding risk, i.e., it improves the safety of the treatment. A lower price (possible as a result of the lower amount of protein needed) for the treatment and the improved risk/benefit ratio enables more widespread use of this method resulting in reduction of mortality. In addition, this method simplifies the administration of the novel anticoagulant, thus only offering more convenience but also will permitting more frequent and more effective treatment of patients, thereby saving many lives.

DETAILED DESCRIPTION OF PREFERRED EMBODIMENTS

Example 1

Figure 1:
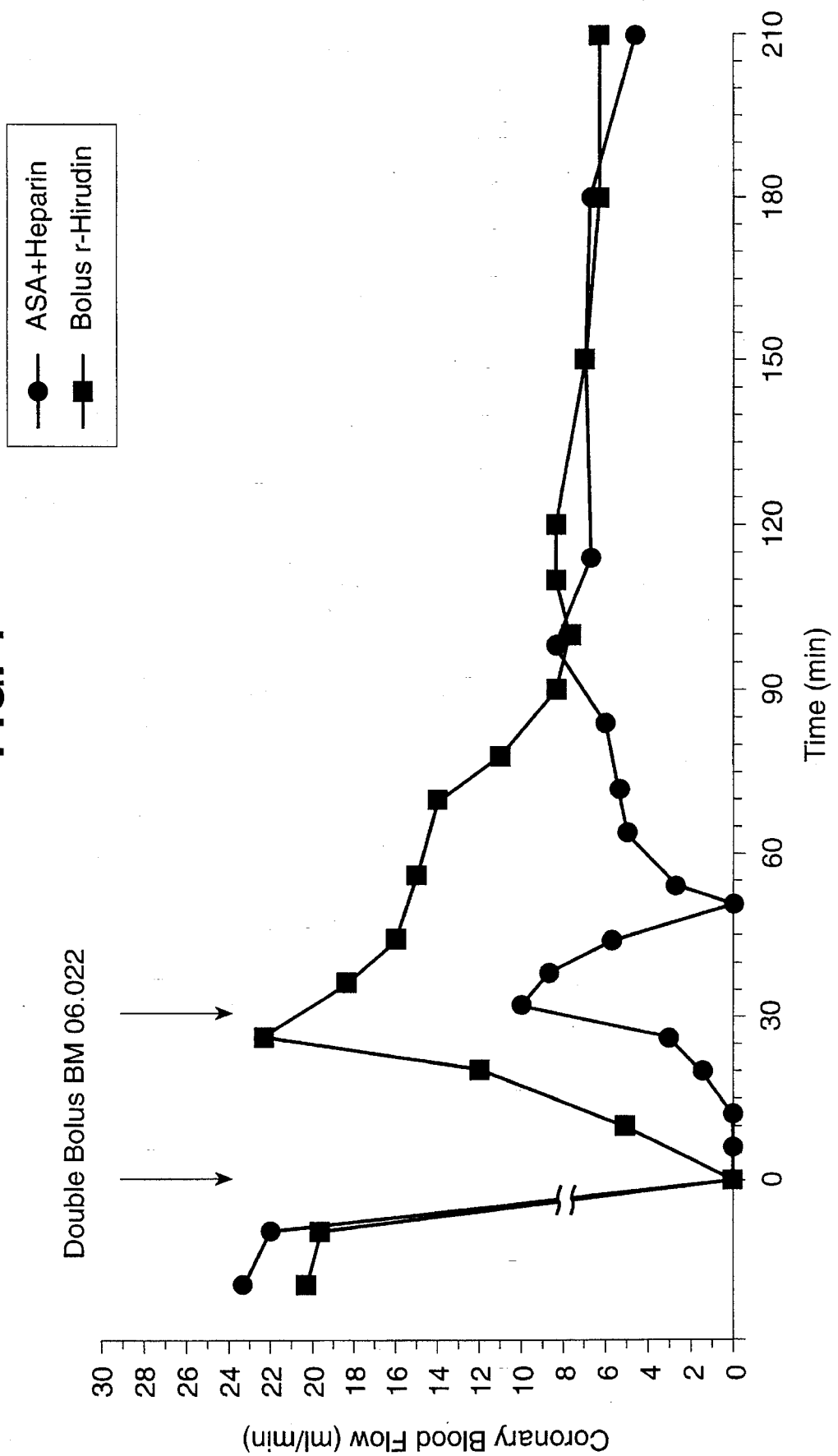
FIG. 1 Time course of coronary blood flow in dogs with coronary arterial thrombosis receiving a double bolus injection of 140 and 140 kU/kg BM 06.022 (SEQ ID NO: 1), 30 min apart, and conjunctive treatment with acetylsalicylic acid (ASA=aspirin; 20 mg/kg i.v. bolus injection) and heparin (120 IU/kg i.v. bolus, followed by continuous i.v. infusion of 80 IU/kg/h heparin) or with ASA (20 mg/kg i.v. bolus injection) and a single i.v. bolus injection of 6 mg/kg hirudin. Data are mean values of n=3 per group.

The present example provides pharmacological evidence of the surprising and superior effect of pharmaceutically effective compositions and methods for treatment of acute occlusive vascular diseases described herein. The animal model employed in the example simulates acute myocardial infarction induced by acute coronary artery thrombus formation and allows evaluation of the risk of reocclusion after successful thrombolysis and of the bleeding risk.

Adult beagle dogs of either sex were anesthetized with intravenous sodium pentobarbital (35 mg/kg body weight), intubated and artificially ventilated. Femoral and brachial veins were catheterized for drug administration or blood withdrawal, respectively. Arterial blood pressure was measured continuously by way of the right femoral artery. The chest was opened at the left, fifth intercostal space and the heart suspended in a pericardial cradle. A 2-cm section of the left circumflex coronary artery was isolated and instrumented as recently described (Martin et al., J Cardiovasc Pharmacol 1991; 18: 111–119). An electromagnetic flow probe was used for continuous blood flow monitoring. Blood pressure, heart rate and coronary blood flow were recorded continuously on a polygraph.

A left circumflex coronary arterial thrombus was produced as follows: an adjustable screw occluder on the left circumflex coronary artery was tightened to produce 90% inhibition of the hyperemic blood flow response to a 20-s occlusion of the coronary artery. A 150 µA continuous anodal current was applied to the coronary artery electrode placed in the lumen of the artery and attached to the inner surface of the coronary artery and maintained until left circumflex coronary arterial blood flow decreased to and remained at 0 ml/min for at least 3 min. Electrical stimulation was delivered for at least 15 min. The thrombus was allowed to age for one hour before the thrombolytically active protein was administered.

The thrombolytically active protein used for thrombolysis in this example was BM 06.022 (SEQ ID NO: 1) disclosed in U.S. Pat. No. 5,223,256. The specific activity of BM 06.022 used in this experimental study was 575 000 U/mg. The anticoagulant used was recombinant hirudin produced in *Hansenula polymorpha* (variant BK-HV).

Adjunctive treatment in the reference group was performed with aspirin and heparin. Aspirin was given as an i.v. bolus injection of 20 mg/kg 45 min after thrombus formation, i.e., 15 min before administration of the thrombolytically active protein. Five min later (i.e., 50 min after thrombus formation= 10 min before administration of the thrombolytically active protein), heparin was administered as an i.v. bolus injection of 120 IU/kg immediately followed by an continuous i.v. infusion of 80 IU/kg/h of heparin.

Adjunctive treatment in the test group was performed with aspirin and hirudin BK-HV. Aspirin was given as an i.v. bolus injection of 20 mg/kg 45 min after thrombus formation, i.e., 15 min before administration of the thrombolytically active protein. Five minutes later (i.e., 50 min after thrombus formation=10 min before administration of the thrombolytically active protein), hirudin BK-HV was administered as an i.v. bolus of 6 mg/kg over 1 min.

A control experiment was performed with aspirin and hirudin BK-HV infusion. Aspirin was given as an i.v. bolus injection of 20 mg/kg 45 min after thrombus formation, i.e., 15 min before administration of the thrombolytically active protein. Five min later (i.e., 50 min after thrombus formation=10 min before administration of the thrombolytically active protein), hirudin BK-HV was administered as an i.v. bolus injection of 2 mg/kg immediately followed by a continuous i.v. infusion of 2 mg/kg/h of hirudin BK-HV.

All dogs received a double bolus injection of the thrombolytically active protein BM 06.022 (SEQ ID NO: 1). The first i.v. bolus injection was performed 60 min after thrombus formation. The second i.v. bolus injection was performed 30 min later, i.e., there was a time interval of 30 minutes between the bolus injections. Each i.v. bolus injection was given at a dose of 140 kU/kg, i.e., the total dose of BM 06.022 was 280 kU/kg.

The experimental observation period was 3.5 h after the first i.v. bolus injection of BM 06.022. Mean and phasic coronary blood flow were measured. The time to reperfusion was defined as the time from onset of thrombolytic treatment to the time of return of coronary blood flow to 33% of the control level before occlusion. Cyclical flow reductions were defined as the number of cycles with reperfusion followed by complete reocclusion (zero flow). Plasma samples were obtained before administration of the adjunctive agents and repeatedly after onset of thrombolytic treatment for measurement of the activated partial thromboplastin time (aPTT) according to Larrieu et al. (Rev Hematol 1957; 12: 199–210) with a test kit from Boehringer Mannheim, Mannheim Germany. Bleeding time was measured with a spring-loaded device (Simplate I from Organon Teknika, Eppelheim, Germany) on the buccal mucosa of the inner lip of the dogs. Incisions were made with the Simplate I device on the mucous membrane of the inner lip of the dog, and the duration of bleeding was timed.

All dogs in these representative experiments demonstrated reperfusion. The conjunctive treatment with aspirin plus bolus hirudin achieved faster reperfusion than with aspirin and heparin-infusion (Table 1: 15 min vs. 25 min). The time to reperfusion after BM 06.022 (SEQ ID NO: 1) plus aspirin and bolus hirudin was comparable to that seen in the control experiment with BM 06.022 plus aspirin and hirudin-infusion. Therefore, a single i.v. bolus injection of hirudin achieved the same degree of fast reperfusion as hirudin-infusion (15 min and 14 min, respectively).

Figure 2:
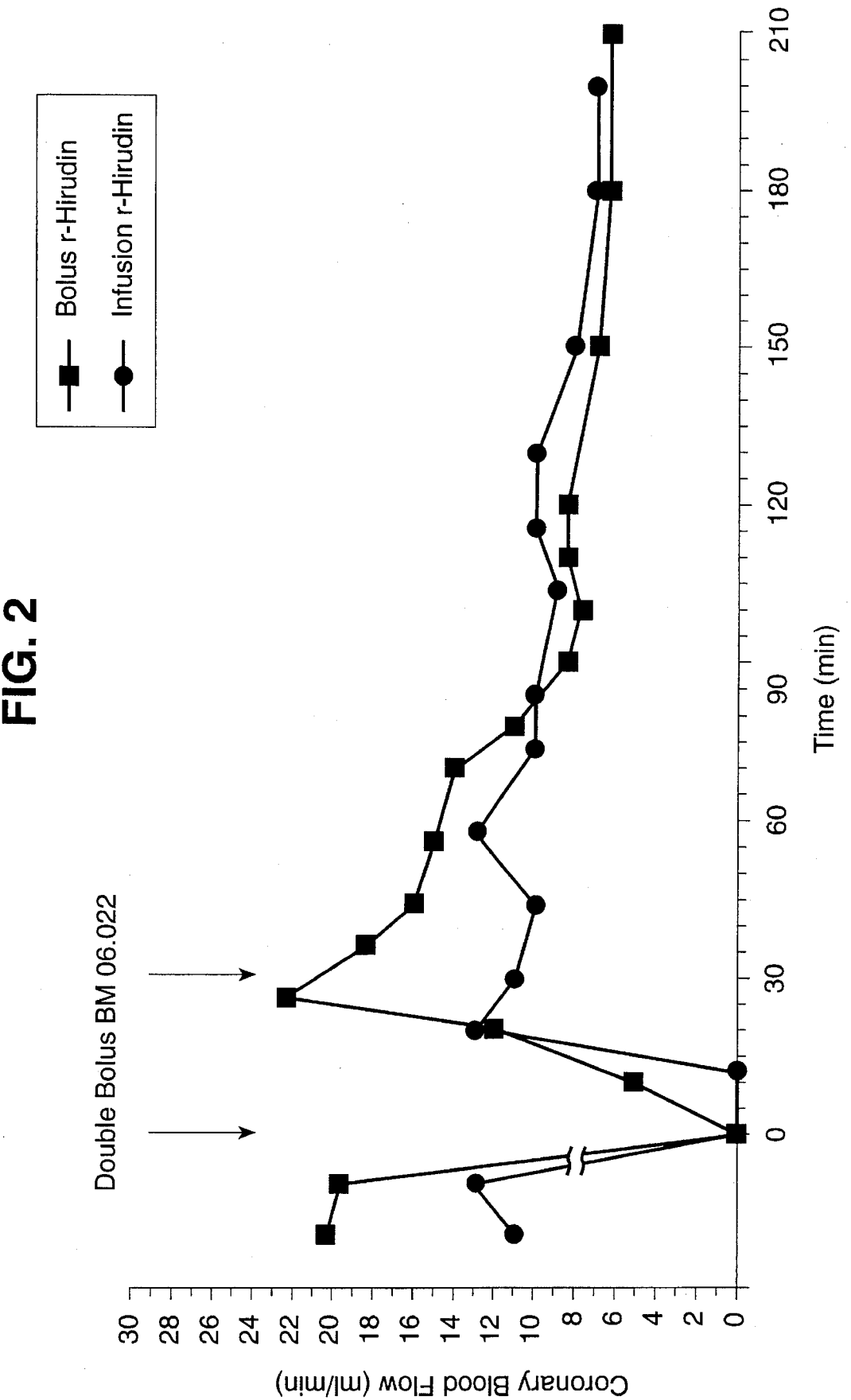
FIG. 2 Time course of coronary blood flow in dogs with coronary artery thrombosis receiving a double bolus injection of 140 and 140 kU/kg BM 06.022 (SEQ ID NO:1), 30 min apart, and conjunctive treatment with acetylsalicylic acid (ASA=aspirin; 20 mg/kg i.v. bolus injection) and hirudin (2 mg/kg i.v. bolus, followed by continuous i.v. infusion of 2 mg/kg/h hirudin) or with ASA (20 mg/kg i.v. bolus injection) and a single i.v. bolus injection of 6 mg/kg hirudin. Data are mean values of n=1 or n=3, respectively, per group.
Figure 3:
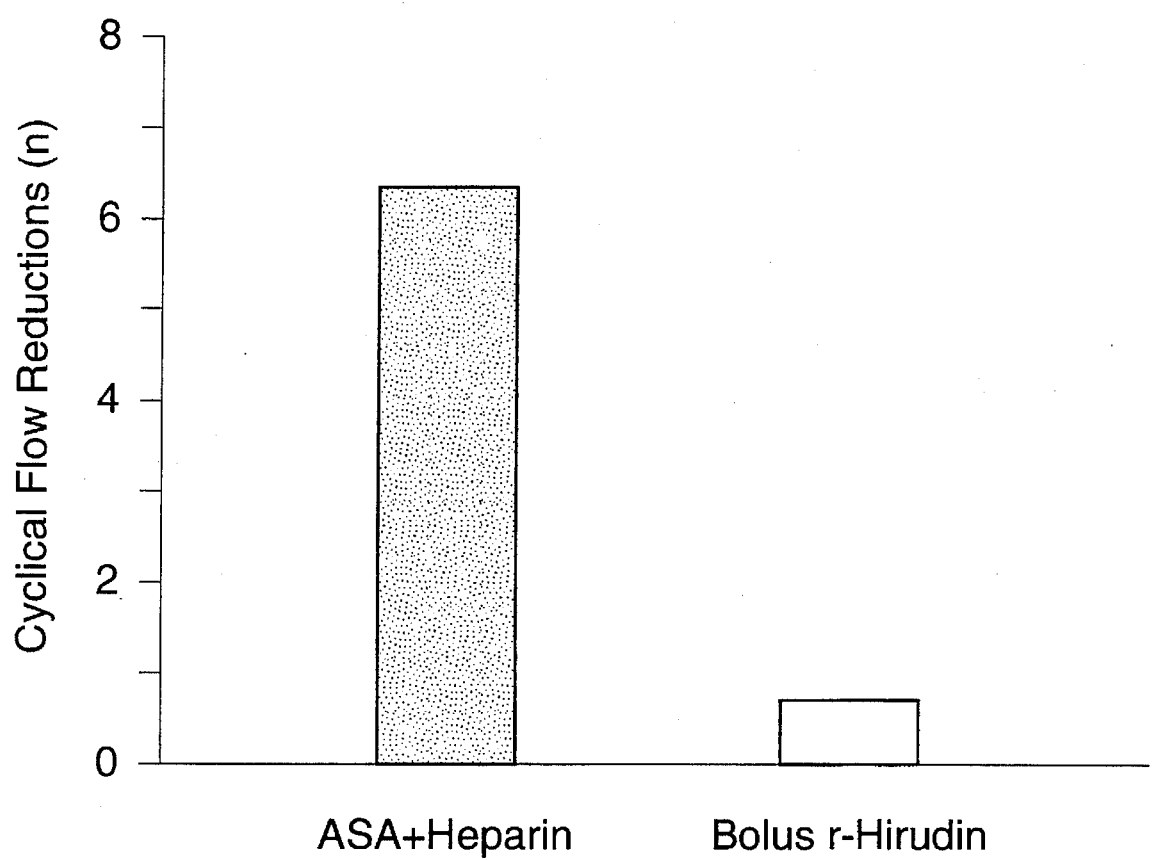
FIG. 3 Number of cyclical flow reductions as an indicator of reocclusion after successful reperfusion in dogs with coronary arterial thrombosis receiving a double bolus injection of 140 and 140 kU/kg BM 06.022, 30 min apart, and conjunctive treatment with acetylsalicylic acid (ASA=aspirin; 20 mg/kg i.v. bolus injection) and heparin (120 IU/kg i.v. bolus, followed by continuous i.v. infusion of 80 IU/kg/h heparin) or with ASA (20 mg/kg i.v. bolus injection) and a single i.v. bolus injection of 6 mg/kg hirudin. Data are mean values of n=3 per group.

In addition, aspirin plus i.v. bolus injection of hirudin was sufficient to convincingly prevent reocclusion in contrast to aspirin plus heparin-infusion as can be seen in FIG. 1, illustrating the time course of coronary blood flow of these two groups. The effects of aspirin plus bolus hirudin in preventing reocclusion were equivalent to those of aspirin plus hirudin-infusion (FIG. 2). Accordingly, aspirin plus bolus injection of hirudin dramatically reduced the number of cyclical flow reductions compared to aspirin plus heparin-infusion (FIG. 3, Table 1) from 6.3 to 0.6 cyclical flow reductions. Bolus hirudin was equivalent to hirudin-infusion (Table 1) in reducing cyclical flow reductions.

Figure 4:
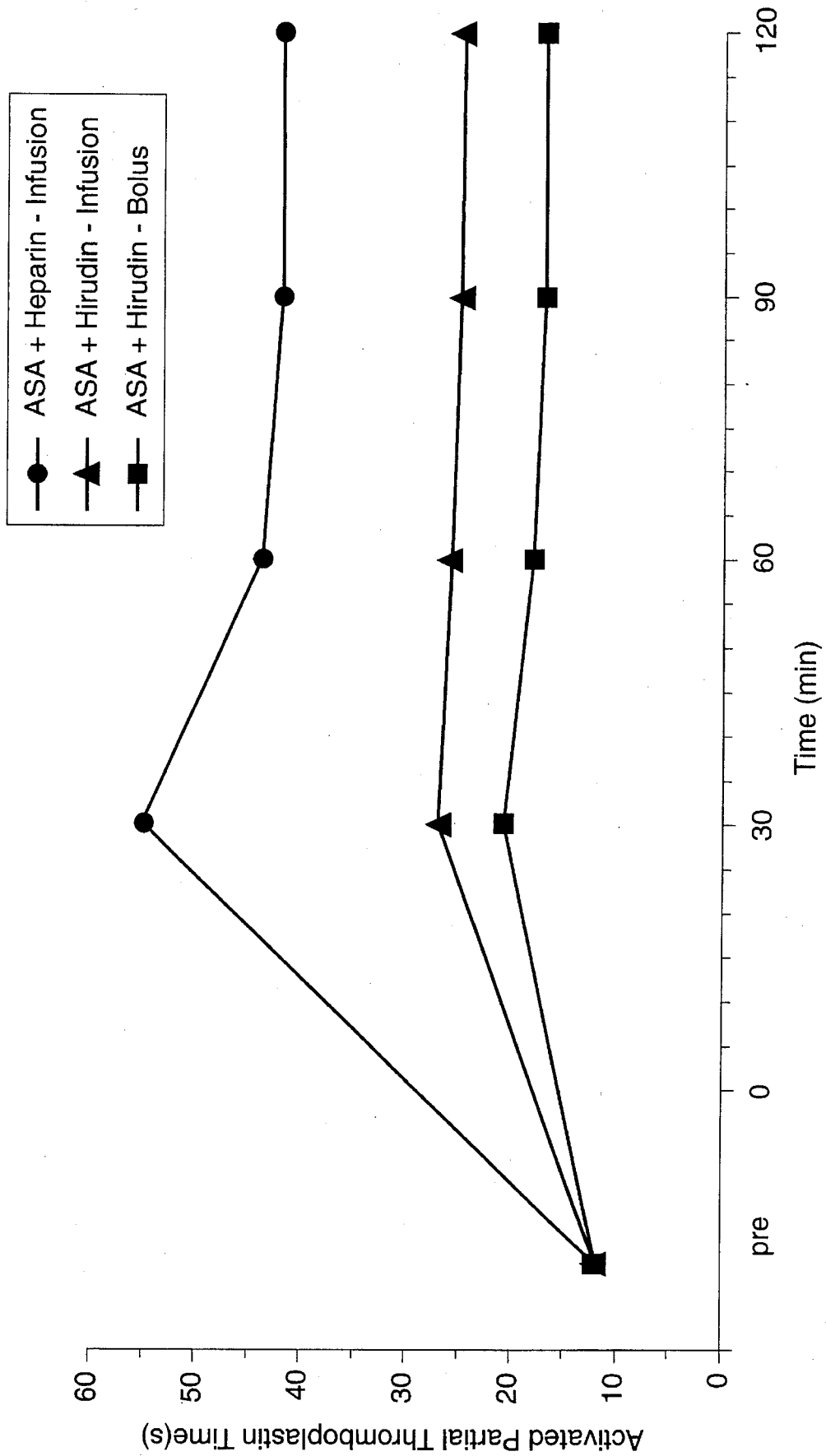
FIG. 4 Time course of activated partial thromboplastin time (aPTT) as an indicator of safety in dogs with coronary arterial thrombosis receiving a double bolus injection of 140 and 140 kU/kg BM 06.022, 30 min apart, and conjunctive treatment with acetylsalicylic acid (ASA=aspirin; 20 mg/kg i.v. bolus injection) and heparin (120 IU/kg i.v. bolus, followed by continuous i.v. infusion of 80 IU/kg/h) or with acetylsalicylic acid (ASA=aspirin; 20 mg/kg i.v. bolus injection) and hirudin (2 mg/kg i.v. bolus, followed by continuous i.v. infusion of 2 mg/kg/h hirudin) or with ASA (20 mg/kg i.v. bolus injection) and a single i.v. bolus injection of 6 mg/kg hirudin. Data are mean values of n=3 or n=1, respectively, per group.

Administration of hirudin either as a bolus or as an infusion induced a lower prolongation of the activated partial thromboplastin time (aPTT) than heparin-infusion (FIG. 4). When the effects of hirudin-bolus on aPTT are compared with those of hirudin-infusion on aPTT, it becomes evident that bolus-hirudin prolonged aPTT at a lower degree than hirudin-infusion (138 vs. 203% of pre-treatment value at 2 h) as found in the present experiments (Table 2). Comparison of the aPTT effects after bolus-hirudin with published experience of the combination of BM 06.022 (SEQ ID NO: 1) plus hirudin-infusion (Martin et al. Int J Hematol 1992; 56: 143–153) confirms the lower prolongation of the aPTT after bolus-hirudin (Table 2).

Figure 5:
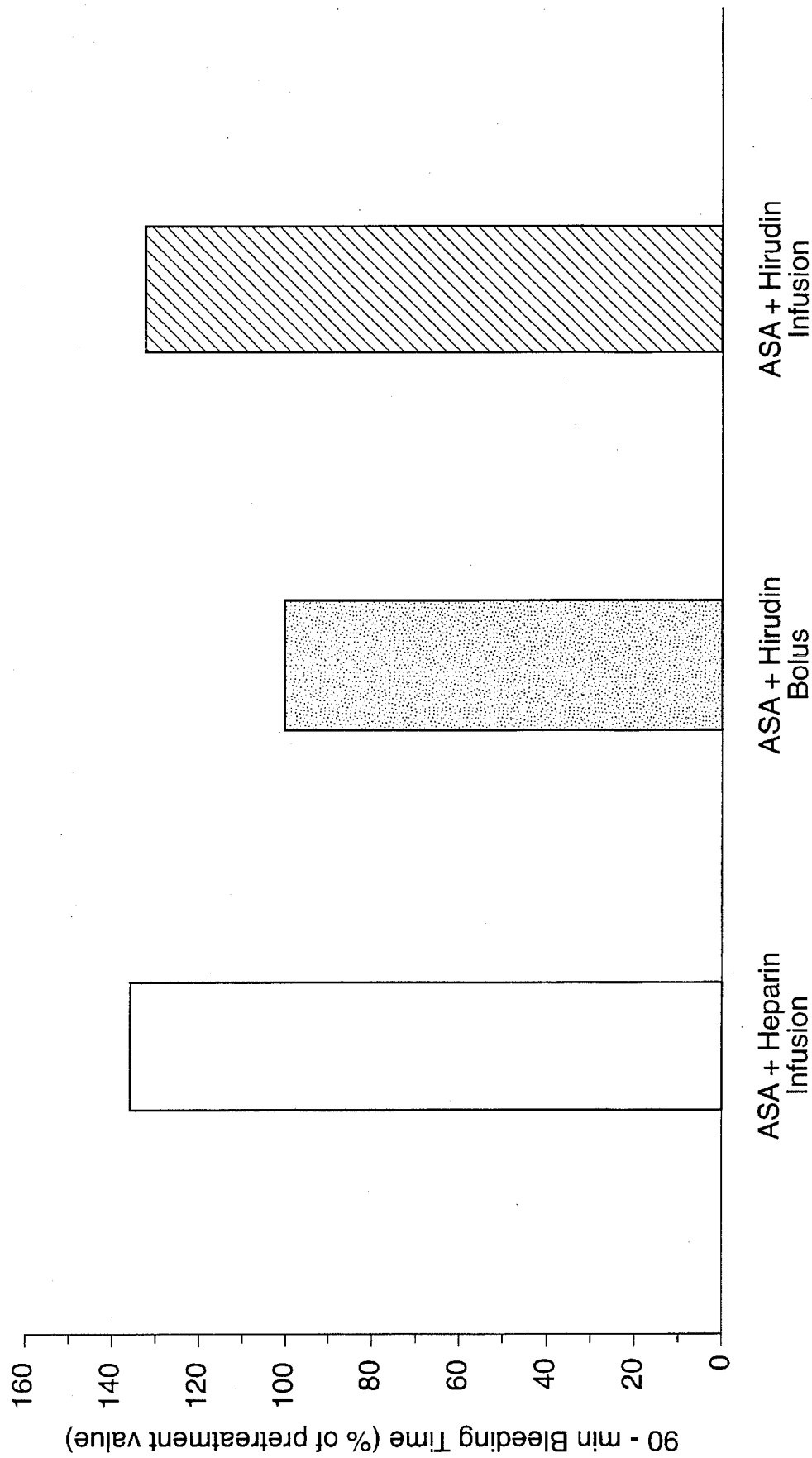
FIG. 5 Bleeding time at 90 min (as % of the pretreatment value) as an indicator of safety in dogs with coronary arterial thrombosis receiving a double bolus injection of 140 and 140 kU/kg BM 06.022 (SEQ ID NO: 1), 30 min apart, and conjunctive treatment with acetylsalicylic acid (ASA=aspirin; 20 mg/kg i.v. bolus injection) and heparin (120 IU/kg i.v. bolus, followed by continuous i.v. infusion of 80 IU/kg/h heparin) or with acetylsalicylic acid (ASA=aspirin; 20 mg/kg i.v. bolus injection) and hirudin (2 mg/kg i.v. bolus, followed by continuous infusion of 2 mg/kg/h hirudin) or with ASA (20 mg/kg i.v. bolus injection) and a single i.v. bolus injection of 6 mg/kg hirudin. Data are mean values of n=3 or n=1, respectively, per group.

The 90-min bleeding time was reported to be a strong predictor of clinical bleeding (Gimple et al., Circulation 1989; 80: 581–588). The present experiments surprisingly showed that bleeding time after bolus-hirudin was less prolonged compared with the pretreatment value than after heparin-infusion as well as after hirudin-infusion (100 vs. 135 or 133%, respectively; Table 3 and FIG. 5). The difference in bleeding time prolongation between bolus-hirudin and hirudin-infusion is also apparent when compared with published reports of the combination of BM 06.022 and hirudin-infusion (Martin et al., Int J Hematol 1992; 56: 143–153; Table 3).

The experimental results discussed herein and comparison of the results with published data demonstrate that a single i.v. bolus injection of hirudin in combination with BM 06.022 can achieve superior effects in accelerating reperfusion and preventing reocclusion as compared to heparin-infusion, comparable to results using continuous i.v. infusion of hirudin in combination with BM 06.022(SEQ ID NO: 1). Favorably, the restriction of the administration of hirudin to a single i.v. bolus injection instead of a continuous i.v. infusion leads to greater therapeutic safety as is evidenced by lower prolongation and more rapid normalization of the aPTT, as well as by lower prolongation of the 90-min bleeding time. In addition, the restriction of the administration of hirudin to a single i.v. bolus injection in this experimental setting (220 min infusion) helped to save 35% of the hirudin amount necessary to achieve the described pharmacologic effects in comparison with hirudin-infusion.

TABLE 1

EFFICACY
Efficacy after administration of BM 06.022 plus conjunctive agents

| Conjunctive agents | N | Incidence of reperfusion* | Time to reperfusion (min) | Cyclical flow reductions (n) |
| --- | --- | --- | --- | --- |
| ASA + heparin-infusion | 3 | 3/3 | 25 | 6.3 |
| ASA + hirudin-bolus | 3 | 3/3 | 15 | 0.6 |
| ASA + hirudin-infusion | 1 | 1/1 | 14 | 1 |

Mean values; *, n of reperfused dogs/n of total dogs.

TABLE 2

SAFETY
Activated partial thromboplastin time (aPTT) after BM 06.022 bolus injections plus conjunctive agents

| | | aPTT | | |
| --- | --- | --- | --- | --- |
| | | (sec) | | (% of pretreatment value) |
| Conjunctive agents | N | pre | 2 h | at 2 h |
| ASA + heparin- infusion | 3 | 12 | 42 | 360 |
| ASA + hirudin- bolus | 3 | 12 | 17 | 138 |
| ASA + hirudin-infusion | 1 | 12 | 25 | 203 |
| Literature: hirudin-infusion | 7 | — | — | 767 | aPTT, activated partial thromboplastin time; pre, pretreatment value. Mean values.
Literature: Martin et al., int J Hematol 1992; 56:143–153 (study about the combination of BM 06.022 plus hirudin-infusion in the same canine model).

TABLE 3

SAFETY
Bleeding time (BT) after BM 06.022 bolus injections plus conjunctive agents

| | | BT | | |
| --- | --- | --- | --- | --- |
| | | (min) | | (% of pretreatment value) |
| Conjunctive agents | N | pre | 90 min | at 2 h |
| ASA + heparin- infusion | 3 | 2.0 | 2.7 | 135 |
| ASA + hirudin- bolus | 3 | 2.33 | 2.33 | 100 |
| ASA + hirudin-infusion | 1 | 1.5 | 2.0 | 133 |
| Literature: hirudin-infusion | 7 | — | 6.9 | — |

BT, bleeding time; pre, pretreatment value. Mean values.
Literature: Martin et al., int J Hematol 1992; 56:143–153 (study about the combination of BM 06.022 plus hirudin-infusion in the same canine model).

As demonstrated, supra, a single intravenous bolus injection over 1 min of 6 mg/kg hirudin to dogs prior to administration of the thrombolytically active protein achieved superior effects compared to conventional anticoagulant therapy with heparin intravenous infusion in preventing reocclusion after successful thrombolysis. Prior art showed that hirudin is concomitantly administered in experimental studies in dogs with coronary artery thrombosis in doses of 6 mg/kg/h infusion (in combination with t-PA: Sitko et al., Circulation 1992; 85: 805–815) or of 2 mg/kg initial i.v. bolus injection plus 2 mg/kg/h i.v. infusion (in combination with streptokinase: Rigel et al., Circ Res 1993; 72: 1091–1102) to achieve superior effects to the control group with heparin infusion. Given a 3.5-h experimental observation period in the dog studies the following amounts of hirudin are required assuming a body weight of 10 kg for a dog:

| Study | Thrombolytic agent | Dose of hirudin over 3.5 h | | Total amount (mg) |
|---|---|---|---|---|
| | | Bolus (mg) | Infusion (mg) | |
| Present invention | BM 06.022 | 60 | — | 60 |
| Rigel et al. | Streptokinase | 20 | 70 | 90 |
| Sitko et al. | t-PA | — | 210 | 210 |

This comparison clearly demonstrates that even during a short observation period of 3.5 h the bolus administration of hirudin reduces the amount of hirudin by a factor of 1.5 or 3.5, respectively. This reduced amount of hirudin was sufficient to achieve the pharmacologic effect of prevention of reocclusion which is superior to that of heparin but comparable to that of hirudin-infusion. Clinical trials with hirudin as described in the background and prior art cited supra infused hirudin for 36, 48, or 96 h which would dramatically increase the difference between the desired amounts necessary for an initial bolus injection and that necessary for continuous i.v. infusion.

It has to be kept in mind that the absolute doses of hirudin in humans are lower than those in dogs because of increased sensitivity (approximately a factor of 10) of human thrombin for inhibition by hirudin. Neuhaus et al. (Circulation 1993; 88 (suppl. I): I-292, abstract 1563) administered hirudin in the form of an initial i.v. bolus injection of 0.4 mg/kg followed by a continuous i.v. infusion of 0.15 mg/kg over 48 h. Cannon et al. (J Am Coll Cardiol 1993; 21: 136A) administered hirudin by an initial i.v. bolus injection of 0.6 mg/kg followed by an i.v. bolus infusion of 0.2 mg/kg over 36 h. However, the relative differences between the regimens (bolus hirudin versus bolus plus infusion hirudin) remained constant in each species.

The present invention relates to therapeutic or prophylactic compositions and methods for treating or preventing thrombotic diseases. More particularly, the present invention relates to pharmaceutically effective compositions and methods for treatment or prophylaxis of thrombotic diseases characterized by the combined administration of an anticoagulant agent different from heparin, given by i.v. bolus injection instead of prolonged i.v. infusion, and a thrombolytically active protein given by i.v. bolus injection and/or i.v. infusion.

Anticoagulants different from heparin encompassed by the present invention include peptidic and synthetic direct inhibitors of thrombin and inhibitors of other components of the coagulation system, such as inhibitors of factor XIIIa, Xa, IXa, VIIa, tissue factor, von Willebrand factor (glycoprotein Ib) etc., or mimics or recombinant forms of endogenous inhibitors of the coagulation system, e.g. thrombomodulin or activated protein C.

These are preferably proteins, peptides, or low molecular weight chemical entities which are produced by recombinant DNA technology, by isolation and purification of substances from natural sources, by peptide synthesis, chemical modification, or by conventional chemical synthesis.

Preferred anticoagulants are natural forms of hirudin (Markwardt, Methods Enzymol 1970; vol. 19:924–932 and Markwardt, Biomed Biochim Acta 1985; 44: 1007–1013), more particularly, recombinant forms of hirudin such as desulfatohirudin (which lacks the sulfate on the tyrosine 63 residue of natural hirudin but has the same amino acid sequence as natural hirudin) (variant 1), CGP 39393 (Thromb Haemost 1989; 61: 77–80), or forms which differ from natural hirudin in amino acid 1 and 2, leucine and threonine such as HBW 023 (Markwardt et al., Thromb Res 1988; 52: 393–400 and Röthig et al., Hämostaseologie 1991; 11: 132–136). Desulfatohirudin can be produced in eukaryotic cells, e.g., *Saccharomyces cerevisiae,* or in bacterial cells, e.g., *Escherichia coli.* Other useful cell lines include *Bacillus subtilis,* baby hamster kidney cells, insect cells and others. Hirudin and desulphatohirudin consist of a single polypeptide chain of 65 amino acids with three disulfide bridges, and have a molecular weight of about 7,000.

The present invention also relates to modified forms of hirudin such as deletion or substitution variants of hirudin and to chimeric or chemically conjugated variants, e.g. PEG-hirudin or PEG-hirudin fragments. The present invention is also particularly related to hirulog and hirulog-like peptides (Maraganore et al., Biochemistry 1990; 29:7095–7101 and Bourdon et al., FEBS letters 1991; 294: 163–166). Hirulog is a 20 amino acid synthetic peptide thrombin inhibitor (D-Phe-Pro-Arg-Pro-[Gly]$_4$ coupled to residues 53–64 of the HV2 hirudin variant).

Hirudin and hirulog, as well as related peptide forms, act by direct and specific inhibition of thrombin. The present invention also relates to synthetic low molecular weight direct thrombin inhibitors useful as anticoagulants such as Argatroban (= MD-805 and MCI-9038) (Clarke et al., Circulation 1991; 83: 1510–1518), GYKI-14766 (=LY 294468) (Jackson et al., J Pharm Exp Ther 1992; 261: 546–552), DuP 714 (Knabb et al., Thromb Haemost 1992; 67: 56–59) or other peptides such as boroarginine (Kettner et al., J Biol Chem 1990; 265: 18298–18297) or SDZ 217766 (Tapparelli and Metternich, Thromb Haemost 1993; 69: 668, abstract 455). Other direct synthetic thrombin inhibitors are derivatives of 3-amidinophenylalanine (Stürzebecher et al., Thromb Haemost 1993; 69: 1316, abstract 2773), or the novel Thrombin-Inhibitor "RTI" (Tschopp et al., Thromb Haemost 1993; 69: 668, abstract 456), and other synthetic direct thrombin inhibitors.

Preferred anticoagulants also include natural and particularly recombinant forms of selective, tight-binding inhibitors of blood coagulation factor Xa, such as Antistasin (Nutt et al., Arch Biochem Biophys 1991; 285: 37–44), and natural and recombinant forms of slow, tight-binding inhibitors, specific for factor Xa, such as tick anticoagulant peptide (Waxman et al., Science 1990; 248: 593–596) and other peptide inhibitors of factor Xa. Factor Xa can also be inhibited by DX-9065a, an orally active synthetic anticoagulant with a benzamidine type structure (Kim et al., Thromb Haemost 1993; 69: 672, abstract 471) and by other synthetic, direct inhibitors of factor Xa.

Inhibitors of factor IXa (e.g., Benedict et al., J Clin Invest 1991; 88: 1760–1765), of factor XIIIa (e.g., Shebuski et al., Blood 1990; 75: 1455–1459), inhibitors of factor VIIa, (e.g., Meluch et al., Thromb Haemost 1993; 69: 887, abstract 1244), of tissue factor, (e.g., Ragni et al., Circulation 1993; 88 (suppl. I): I-615, abstract 3309), of glycoprotein Ib, or von Willebrand factor, (e.g., Yao et al., Clinical Research 1993; 41: 228A) and other inhibitors of components of the coagulation system are also included in the invention. Other anticoagulants useful in the invention are mimics or recombinant forms of endogenous inhibitors of the coagulation system such as recombinant thrombomodulin (e.g., Gomi et al., Blood 1990; 75: 1396–1399), recombinant tissue factor pathway inhibitor (e.g., Haskel et al., Circulation 1991; 84: 821–827), recombinant activated protein C (e.g., Gruber et al., Circulation 1990; 82: 578–585) and other mimics of endogenous anticoagulants.

The anticoagulants of the invention are administered in doses of 0.01 to 10 mg/kg over 0.5 to 5 minutes as an intravenous bolus injection prior to or shortly after initiation of administration of the thrombolytically active protein. Hirudin, hirulog and related peptides are preferably administered in doses of 0.3 to 6 mg/kg over 0.5 to 3 min as intravenous bolus injections prior to or within 5 min after initiation of administration of the thrombolytically active protein. More particularly, hirudin, hirulog and related peptides are administered in doses of 0.5 to 6 mg/kg over 1-2 min as intravenous bolus injections prior to administration of the thrombolytically active protein. Oral administration instead of intravenous bolus injection can be performed with low molecular weight forms of new chemical entities and with peptides in combination with drug delivery systems.

Thrombolytically active proteins useful in combination with the anticoagulants in the present invention are those agents known to the skilled artisan, such as recombinant tissue-type plasminogen activator, e.g., Alteplase and silteplase, and others such as anistreplase, streptokinase, urokinase, and pro-urokinase. The present invention also relates to thrombolytic agents such as recombinant plasminogen activator (rPA), BM 06.022 (SEQ ID NO: 1), vampire bat plasminogen activator (e.g., Mellott et al., Arterioscler Thrombos 1992; 12: 212–221) and desmodus (vampire bat) salivary plasminogen activator DSPA (e.g., Witt et al., Blood 1992; 79: 1213–1217) or related forms, and TNK variants of tissue-type plasminogen activator (e.g., Refino et al., Thromb Haemost 1993; 69: 841, abstract 1074). Especially preferred is the thrombolytically active protein BM 06.022 described supra. This is a non-glycosylated protein consisting of amino acids 1-3 and 176-527 of wild type human t-PA. Additional thrombolytically active proteins are described in U.S. Pat. No. 4,970,159; EP-A-0,207,589; AU 61804/86; EP-A-0,231,624; EP-A-0,289,508; JP 63133988; EP-A-0,234,051; EP-A-0,263,172; EP-A-0,241,208; EP-A-0,292,009; EP-A-297,066; EP-A-0,302,456; EP-A-0,379,890. All may be used in this invention, as can E-6010 (Suzuki et al., J Cardiovasc Pharmacol 1991; 17: 738–746), YM-866 (Kawasaki et al., Japan J Pharmacol 1993; 63: 135–142) and SUN-9216 (Umemura et al., Stroke 1993; 24: 1077–1082). Additional useful thrombolytically active proteins include LY 210825 (=K2P from Syrian hamster cells; Circulation 1990; 82: 930–940), FE3X and FE1X (=K1K2P from Chinese hamster ovary cells, Blood 1988; 71: 216–219), FEK1 (K2P from mouse C127 cells, J Cardiovasc Pharmacol 1990; 16: 197–209), t-PA variants (Thromb Haemost 1989; 62:542), K2P and D-K2P (Thromb Haemost 1989; 62: 393), MB-1018 (FK2K2P), Thromb Haemost 1989; 62: 543), FK2P (FASEB J 1989; 3: A1031, abstract 4791), 1X (Circulation 1988; 78: II-15, abstract 59), K1K2P (Thromb Res 1988; 50: 33–41), FK1K2P (J Biol Chem 1988; 263: 1599–1602).

The doses and administration regimens of the thrombolytic agents include those approved by the health authorities, e.g. 100 mg of Alteplase or 1.5 million U of streptokinase. The dose and administration regimen can vary. Especially preferred is a total dose of 15 to 25 mega units (MU) of recombinant plasminogen activator BM 06.022 (SEQ ID NO: 1); more especially preferred is a regimen of 10+10 MU boli of BM 06.022. The mode of administration of the thrombolytic agents may be via intravenous injection or via intravenous infusion, or a combination of these. Especially preferred is a double bolus intravenous injection of BM 06.022 or of other thrombolytically active proteins. The time interval between the injections of the thrombolytically active protein may be from 15 to 60 min, more preferably from 20 to 40 min, most preferably the time interval may be 30 min.

The combination of hirudin as the novel more potent and effective anticoagulant different from heparin by i.v. bolus injection with BM 06.022 as the thrombolytically active protein at dosing regimens described above is particularly preferred. The combination of hirulog as the novel more potent and effective anticoagulant different from heparin by i.v. bolus injection with BM 06.022 as the thrombolytically active protein at dosing regimens described above is also preferred.

The administration of the non-heparin anticoagulant as a single i.v. bolus injection may be followed 1 to 2 hours later by standard treatment with heparin in the treatment of acute myocardial infarction, i.e., i.v. infusion of heparin and later by subcutaneous administration, or may be followed directly by subcutaneous administration of heparin.

The present approach of administering a non-heparin anticoagulant includes administration of antiplatelet agents different from aspirin (acetylsalicylic acid). Anticoagulant, as well as antiplatelet agents clinically act as antithrombotic agents but differ in their mode of action, i.e., both actions (inhibition of coagulation and inhibition of platelets) prevent thrombus formation and reocclusion. Antiplatelet agents different from aspirin are given as a single i.v. bolus injection, concomitantly with the thrombolytically active protein, i.e., prior to or within 30 min of administration of the thrombolytically active protein, and may be followed by administration of aspirin over several days instead of by delayed or prolonged administration of the novel more potent and effective antiplatelet agent.

The novel more potent and effective antiplatelet agents different from heparin are preferably inhibitors of the glycoprotein IIb/IIIa receptor on platelets which mediates platelet aggregation. Such inhibitors of the platelet glycoprotein IIb/IIIa (GP IIb/IIIa) receptor may be antibodies, fragments of antibodies, humanized antibodies or humanized fragments of antibodies to the GP IIb/IIIa receptor, peptides or peptidomimetics acting as antagonists to the GP IIb/IIIa antagonist, and low molecular synthetic new chemical entities inhibiting the GP IIb/IIIa antagonist.

Inhibitors of the GP IIb/IIIa receptor are preferably the monoclonal antibody 7E3 or chimeric 7E3 antibody (fragment) to GP IIb/IIIa (Tcheng et al., Circulation 1993; 88 (suppl. I): I-506, abstract 2727), the peptide GP IIb/IIIa antagonists Integrelin (Tcheng et al., Circulation 1993; 88 (suppl. I): I-595, abstract 3200) and the peptide MK-852 (Theroux et al., Circulation 1993; 88 (suppl. I): I-201, abstract 1075), as well as the nonapeptide mimic of GP IIb/IIIa, MK-383 (Peerlinck et al., Circulation 1993; 88: 1512–1517).

Further antagonists of the GP IIb/IIIa receptor include Ro 43-5054 (J Pharmacol Exp Ther 1993; 264: 501–508), Ro 44-9883 (Thromb Haemostas 1993; 70: 817–821), BIBU 104 (Thromb Haemostas 1993; 69: 975, abstract 1557) and BIBU 52 (Thromb Haemostas 1993; 69: 1072, abstract 1887), SC 49992 (J Pharmacol Exp Ther 1993; 267: 1191–1197) and SC 54684 (Thromb Haemostas 1993; 69: 975, abstract 1558), DMP 728 (Circulation 1994; 80: 3–12), GR 144053 (Thromb Haemostas 1993; 69: 1071, abstract 1884), FR 144633 (Thromb Haemostas 1993; 69: 706, abstract 598), SKF-106760 (Nichols et al. presented at the Am Soc Pharmacol Exp Ther Meeting, Jul. 30–Aug. 3, 1993 in San Francisco, Calif., USA). Some of these inhibitors may be given by a single oral dose instead of a single i.v. bolus injection.

The present invention includes other inhibitors of GP IIb/IIIa not specifically mentioned herein.

Thrombotic diseases in the meaning of the present invention include acute myocardial infarction, stroke, peripheral arterial occlusion, pulmonary embolism, deep vein thrombosis, and other blood vessel thrombotic diseases which have a risk of reocclusion or recurrent thrombus formation after successful thrombolysis.

Treatment of a patient with a thrombotic disease by a composition and method according to the present invention may include concomitant use of further adjunctive agents, such as antiplatelet agents, e.g., aspirin, and anticoagulant agents, e.g., heparin or low molecular weight heparin, or other drugs, e.g., B-blockers, angiotensin converting enzyme inhibitors, agents against reperfusion injury and others.

The present invention provides compositions and methods for treatment of patients with thrombotic diseases which confer the advantages of reducing the amount of novel anticoagulant agents, but maintaining the desired pharmacologic effect, of reducing the costs of therapy, of enhancing convenience of administration of the novel anticoagulant drug and, most importantly reducing the bleeding risk. All of these advantages will considerably contribute to more widespread use of thrombolysis which will help to save more lives.

The advantages of the invention are evident. The convenient administration of the non-heparin anticoagulant different from heparin will contribute to more widespread use, even in the prehospital phase and permits more frequent and more effective treatment of patients, thereby saving many lives.

More importantly, the restriction of the administration of the non-heparin anticoagulant, e.g., hirudin, solely to an i.v. bolus injection instead of initial bolus injection plus continuous i.v. infusion over hours leads to greater safety for the patient by reducing the bleeding risk. The reduced bleeding risk results from a shorter duration of inhibition of the coagulation system, a more rapid normalization of the coagulation system, and a lower influence on the bleeding time. As can be seen in Example 1, the activated partial thromboplastin time (aPTT) which is a measure of the intrinsic part of the coagulation system at 2 h post administration of the thrombolytically active protein (= 3 h+10 min after i.v. bolus injection of the novel anticoagulant hirudin) nearly has returned to pretreatment levels, whereas the aPTT still is considerably prolonged in the group with continuous intravenous infusion of the anticoagulant. This indicates the limited duration of the anticoagulant effect after i.v. bolus injection which was sufficiently long to prevent reocclusion and sufficiently short to avoid bleeding. Accordingly, bleeding time which is a strong predictor of clinical bleeding (Gimple et al., Circulation 1989; 80: 581–588) is considerably lower in the group with i.v bolus injection of the novel anticoagulant than in the group with i.v continuous infusion of the anticoagulant.

Moreover and surprisingly, as can be seen in Example 1, the restriction of administration of the novel anticoagulant solely to an i.v. bolus injection instead as an administration of i.v. bolus injection plus continuous i.v. infusion (bolus plus infusion is prior art) has maintained the superior effect of prevention of reocclusion by use of novel anticoagulants given as i.v. bolus injection plus infusion compared to that of conventional adjunctive treatment with aspirin plus heparin which still is associated with reocclusion.

Other aspects of the invention will be clear to the skilled artisan, and need not be repeated here.

It will be understood that the specification and examples are illustrative but not limitative of the present invention and that other embodiments within the spirit and scope of the invention will suggest themselves to those skilled in the art.

We claims:

1. Method for treating a subject in need of thrombolytic therapy, comprising administering to said subject an effective amount of:
   (i) BM 06.022, which consists of SEQ ID NO: 1 and
   (ii) via bolus injection, hirudin.
2. The method of claim 1, wherein said BM 06.022 is administered intravenously.
3. The method of claim 1, wherein said BM 06.022 is administered in bolus form.
4. The method of claim 1, wherein said BM 06.022 is administered in more than one bolus.
5. The method of claim 4, wherein said boli are administered to said patient about 30 minutes apart.
6. The method of claim 1, further comprising administering a non-aspirin, antiplatelet agent.
7. The method of claim 1, further comprising administering heparin to said subject.
8. The method of claim 5, wherein said two boli comprise doses of 10 MU of BM 06.022.
9. The method of claim 7, wherein said heparin is administered via intravenous infusion, or subcutaneously.
10. The method of claim 7, wherein said heparin is administered 1–2 hours after administration of hirudin.

* * * * *